United States Patent [19]

Geiger et al.

[11] Patent Number: 4,983,511
[45] Date of Patent: Jan. 8, 1991

[54] METHOD AND KIT FOR DETECTING LIVE MICROORGANISMS IN CHLORINE-OR BROMINE-TREATED WATER

[75] Inventors: Jon R. Geiger, West Hartford; Jayne F. Carney, Wolcott; Katherine P. Roberts, Derby, all of Conn.

[73] Assignee: Olin Corporation, Cheshire, Conn.

[21] Appl. No.: 294,842

[22] Filed: Jan. 9, 1989

[51] Int. Cl.$^5$ .......................... C12Q 1/68; C12Q 1/02; C12Q 1/04; G01N 21/76
[52] U.S. Cl. .......................... 435/6; 435/29; 435/34; 435/259; 436/501; 436/94; 436/164; 436/172
[58] Field of Search ................. 435/6, 29, 30, 34, 810, 435/259; 436/94, 164, 172, 805, 808, 501; 536/27, 28; 935/77, 78

[56] References Cited

U.S. PATENT DOCUMENTS

| | | | |
|---|---|---|---|
| 4,670,379 | 6/1987 | Miller | 536/28 |
| 4,683,195 | 7/1987 | Mullis et al. | 435/6 |
| 4,683,202 | 7/1987 | Mullis | 435/91 |
| 4,689,295 | 8/1987 | Taber et al. | 435/34 |
| 4,792,519 | 12/1988 | Blackburn et al. | 435/6 |
| 4,797,480 | 1/1989 | Sorbi et al. | 536/28 |
| 4,816,389 | 3/1989 | Sansonetti et al. | 435/6 |

FOREIGN PATENT DOCUMENTS 0070685 10/1985 European Pat. Off. .

OTHER PUBLICATIONS

Echeverria et al., Journal of Clinical Microbiology, vol. 16, No. 6, pp. 1086–1090, 1982, "Detection of Enterotoxigenic Escherichia coli in Water by Filter Hybridization With Three Enterotoxin Gene Probes".
Saiki et al., "Enzymatic Amplification of B-globin Genomic Sequences and Restriction Site Analysis for Diagnosis of Sickle Cell Anemia", Science, 230, pp. 1350–1354 (1985).
Gerba et al., "Low Cost Rapid Methods for Enterovirus Detection in Water", Technology Conference Proceedings; Advances in Water Analysis and Treatment, Portland, Oregon, pp. 1025–1041, 1986.
Steffan et al., "DNA Amplification to Enhance Detection of Genetically Engineered Bacteria in Environmental Samples", Appl. Environ. Micorbiol., 54, pp. 2185–2191 1988.

*Primary Examiner*—Robert A. Wax
*Assistant Examiner*—Stephane W. Zitomer
*Attorney, Agent, or Firm*—Dale Lynn Carlson

[57] ABSTRACT

Water monitoring systems, and more specifically, to a method and kit for detecting the presence of only living undesirable or indicator microorganisms in water after treatment of the water with chlorine or bromine.

10 Claims, No Drawings

METHOD AND KIT FOR DETECTING LIVE MICROORGANISMS IN CHLORINE- OR BROMINE-TREATED WATER

This invention relates generally to water monitoring systems, and more specifically, to a method and kit for detecting the presence of only living undesirable or indicator microorganisms in water after treatment of the water with chlorine or bromine.

Chlorine is used extensively in the United States and foreign countries to treat drinking water supplies, as well as to treat wastewater and water used in spas, swimming pools, and a variety of industries. The chlorine acts as a biocide to destroy undesirable microorganisms. The efficacy of the chlorine treatment is monitored by periodic checking of the treated water for the presence of selected, living, indicator organisms (e.g., coliforms), or in some cases for specific undesirable microorganisms themselves. Indicator organisms serve to indicate, for example, the possibility of potable water supply contamination. Conventional microorganism detection methods used to monitor the treated water require the growth of the microorganisms in culture media to a detectable level, followed by confirmatory tests for the presence of specific microorganisms. These conventional detection methods may take up to several days to complete.

A more rapid method for detecting the presence of live microorganisms in chlorine-treated water would be extremely useful to water treatment industries. One possible detection technique, namely the use of monoclonal or polyclonal antibodies has been found by the present inventors to be unsuitable for such detection since the antibody techniques do not distinguish between living and dead microorganisms in the chlorine-treated water, as more fully described in co-pending U.S. patent application Ser. No. 115,313, filed Nov. 2, 1987. Since only living cells are potentially harmful, any test which does not distinguish living from dead cells will tend to give a so-called "false-positive" result when only the innocuous dead cells are present. On this basis, antibody techniques are unacceptable for use (as described) by industries or utilities providing or treating chlorinated water.

In light of the foregoing, the discovery of a rapid microorganism detection method for use in chlorine-treated water which selectively detects living microbial cells would be highly desired by a number of industries and utilities providing or treating water.

In one aspect, the present invention relates to a method for detecting the presence of live microorganisms in chlorine- or bromine-treated water comprising:

(a) lysing live microorganisms present in a sample of chlorine- or bromine-treated water and rendering constituent nucleic acid molecules single-stranded to provide a single-stranded target polynucleotide;

(b) contacting said single-stranded target polynucleotide, under hybridization conditions, with first and second single-stranded labelled probe nucleic acid segments which are complementary to mutually exclusive portions of said single-stranded polynucleotide to cause hybridization between said single-stranded target polynucleotide and said first and second single-stranded labelled probe nucleic acid segments, said first and second single-stranded labelled probe nucleic acid segments cooperating after said hybridization to generate or receive a detection signal, and (c) detecting said detection signal to permit identification of said hybridization, whereby a positive detection signal evidences the presence of said live microorganisms in said sample.

In another aspect, the present invention relates to a kit for detecting the presence of live microorganisms in chlorine- or bromine-treated water comprising:

(a) a sample of live microorganisms in, or obtained from, chlorine- or bromine-treated water (and usually provided by the user of the kit), (b) a lysing medium for providing a single-stranded target polynucleotide from within said live microorganisms, (c) first and second single-stranded labelled probe nucleic acid segments which are complementary to mutually exclusive portions of said single-stranded target polynucleotide, said first and second single-stranded labelled probe nucleic acid segments being adapted to cooperate to generate or receive a detection signal after hybridization with said single-stranded target polynucleotide, (d) an (optional) hybridization solution to facilitate rapid hybridization of probe nucleic acid with target nucleic acid, and (e) detection means for identifying said detection signal, whereby a positive detection signal evidences the presence of said microorganisms in said sample.

In accordance with earlier work of the present inventors as disclosed in co-pending U.S. patent application Ser. No. 115,313, it was surprisingly discovered that nucleic acid probes can be used to detect the presence of only living microorganisms (as selectively distinguished from dead microorganisms) in chlorine- or bromine-treated water. This discovery was particularly surprising in view of the findings by the present inventors that antibodies are unsuitable since they do not differentiate living versus dead microorganisms present in chlorine- or bromine-treated water. In addition, nucleic acid probes themselves are not suitable for use with hydrogen peroxide, chlorine dioxide, or chloramine-treated water because nucleic acid probes do not distinguish live killed cells when microorganisms are killed by chlorine dioxide, iodine, or chloramine (as long as free chlorine is not generated during chloramine solution preparation).

By virtue of the present invention, a simplified method and kit are provided which provides for the detection and/or quantification of undesirable or indicator microorganisms without physically separating probes to hybridized target nucleic acid mole molecules from unhybridized probe.

Nucleic acid (DNA or RNA) from undesirable or indicator microorganisms, a portion of whose specific base sequence is generally known, is referred to herein as a target. The polynucleotide containing the label and expected to have a base sequence complementary to the target is referred to herein as a probe. DNA and RNA probes are single-stranded nucleic acid molecules generally synthesized by so-called gene machines or made using recombinant DNA methods. Probes are constructed so that the base sequences of the probe match (and lend themselves to hybridization with) complementary sequences on a target molecule. First and second labelled probe segments which are complementary to mutually exclusive portions of the target polynucleotide are contacted with the target under hybridization conditions.

As used herein, the term "mutually exclusive" means that during hybridization by the first and second probe segments with each target sequence, the two probes should not compete for the same nucleotide base sequence on the target to the extent that hybridization is prevented. In one particular embodiment, spacing of the two DNA probes would have the 3'-terminal nucleotide of the first probe approximately ten bases away from the 5'-terminal nucleotide of the second probe. This will space the termini such that they are on the same side of the helix and thus position the reporter or signal groups attached to the probe nucleic acid in the most favorable position with respect to each other.

The joining together of both target and complementary first and second probe nucleic acid segments by the mechanism of base pairing through hydrogen bonds between purine and pyrimidine bases is thus referred to herein as "hybridization" and the resultant complex is termed a hybridized nucleic acid molecule or hybridized probe/target molecule. After hybridization, the first probe segment and the second probe segment are bound in close proximity to each other on the hybridized moiety. In this proximity, the first and second probe segments are adapted to send or receive a detection signal to make it possible to determine the existence of hybridization and, optionally, to quantify the level of contamination by the living (indicator or undesirable) microorganisms in the water sample, based upon the strength of the detection signal.

The first and second probe nucleic acid segments will typically consist of chemically synthesized or biologically prepared DNA or RNA polynucleotides in the form of single-stranded sequences. If synthesized, the single-stranded DNA or RNA probe is fabricated so that its nucleic acid base sequence is complementary to a region of the bacterial, protozoan, or other microorganisms target sequence.

The first and second probe nucleic acid segments will normally have a minimum of 20 bases, and usually more than 30 bases. Although they may have 10,000 bases or more, 5,000 is usually the maximum. The probe sequence must be substantially complementary to a sequence characteristic of the microorganism of interest. Each probe segment need not have perfect complementarity to the sequence to which it hybridizes; 30 percent or more mismatched pairs, hybridization may still be detected by suitable alteration of hybridization conditions such as the buffer composition and the hybridization temperature.

In accordance with the method of the present invention, the first and second probe segments are respectively labelled with a catalyst-label and a luminescer-label or with two luminescer-labels. The use of such a dual label system is well-known in the art. For example, Heller et al, European patent application No. 82303699.1, Publication No. 0070685, published July 14, 1982, disclose a homogeneous light-emitting hybridization assay wherein luminescer-labelled first and second single-stranded reagent segments are hybridized with a complementary target single-stranded polynucleotide from a sample such that non-radiative energy transfer occurs between the labels of the two reactant segments. At least one of the labels is of the absorber/emitter type and the other is of the chemiluminescent type such that energy in the form of a photon generated by the chemiluminescent light label is re-emitted at a different wavelength. Such secondary emissions can only occur if hybridization has taken place and can be measured at the appropriate wavelength of light emitted by the absorber/emitter.

Likewise, the use of a catalyst-labelled first polynucleotide probe segment in combination with an apoluminescer-labelled second polynucleotide probe segment is disclosed in U.S. Pat. No. 4,670,379. These first and second probe segments are both hybridized with a complementary target polynucleotide sequence in a test sample. A substrate is added to the sample and is converted by the catalyst to a transformation radical which in turn converts the apoluminescer to a luminescer. This occurs if, and only if, the catalyst is juxtaposed closely to the apoluminesor such that the transformation radical can react with the apoluminescer. The sample is irradiated, and the incident light absorbed by the luminescer is re-emitted at a different wavelength. Such secondary emissions can occur only if hybridization has taken place. Hence, the presence of the target polynucleotide is related to the secondary light emitted.

As used herein, "polynucleotide" refers to a polymer of ribonucleic acid (RNA) or deoxyribonucleic acid (DNA), which can be single- or double-stranded.

The complete disclosure of the aforementioned Heller et al European patent and the U.S. Pat. No. 4,670,379 are incorporated herein by reference in their entirety.

Preferred labels for the probe segments include both chemiluminescent and bioluminescent types. As used herein, the term "chemiluminescent" shall include the closely related term "bioluminescent."Chemiluminescent moieties useful within the scope of this invention include catalysts such as peroxidase, bacterial luciferase and firefly luciferase and other chemiluminescent moieties such as functionalized iron-porphyrin derivatives, and others. Choice of the chemiluminescent moiety depends on several factors which include: (1) hybridization conditions to be used, particularly temperature; (2) method to be used for covalent coupling to the ss-polynucleotide reagent segment; and (3) size of the ss-polynucleotide reagent segment. The reagents effective for inducing light emission from the chemiluminescent moieties will depend upon the particular system being used and are well documented in the literature.

As used herein, the term "hybridization conditions" means those conditions which will enable the first and second probes to form stable probe-target hybrids. The proper hybridization conditions will be determined by the nature of the catalyst and apoluminescer employed, the length of the nucleotide polymer of the labelled probes, and the guanosine plus cytosine content of the probes and/or the target polynucleotide.

The term "fluorescent" generally refers to luminescent compounds having the characteristic of re-emitting absorbed incident energy in about $10^{-8}$ to $10^{-3}$ seconds, while the term "phosphorescent" refers to luminescent compounds which take longer to re-emit absorbed incident energy. Also, depending upon the source of incident energy (i.e., photons, charged particles, chemical phenomena, etc.), luminescent compounds are referred to as chemiluminescent, bioluminescent, electroluminescent, photoluminescent, etc.

The term "apoluminescer" refers to any non-luminescent compound which, upon activation by a "transformation radical," converts to a luminescer. Likewise, the term "catalyst" (e.g., an enzyme) as used herein refers to compositions which are capable of releasing an appropriate transformation radical from a substrate for that catalyst.

For example, a hydroxy (OH—) transformation radical can be produced by any of the well-known catalysts (e.g., horseradish peroxidase, hematin, metal cation, especially EDTA-Fe III complexes, microperoxidase, and other redox enzymes) acting upon an appropriate substrate (e.g., molecular oxygen, hydrogen peroxide, HCOOH, $H_3$CCOOH, t-butylhydroperoxide, linoleic hydroperoxide, chlolesterol 5-hydroperoxide and cumen hydroperoxide). The (OH—) radical will then convert the apoluminscer to the corresponding luminescer (e.g., activated diacetyl-dichlorofluorescein to dichlorofluoroscein, homovanillic acid to 2,2'-dihydroxy-3-,3'-dimethoxy-biphenyl--5,5'-diactic acid, p-hydroxyphenylacetic acid to 2,2'-dihydroxybiphenyl-5,5'-diacetic acid, tyrosine to 2,2'-dihydroxybiphenyl-5,5'-diethylamine, luminol to 3-aminophthalic acid plus light, and p-hydroxyphenylpropionic acid to 2,2'-dihydroxybiphenyl-5,5'-dipropionic acid).

These catalysts, substrates and apoluminescers are readily available from many commercial sources.

The choice of the label can be governed by the effect of the label on the rate of hybridization and binding of the probe to the target DNA. It will be necessary that the label provide sufficient sensitivity to detect the amount of DNA available for hybridization. Other considerations will be ease of synthesis of the probe, ready availability of instrumentation, ability to automate, convenience, and the like.

Enzymes useful as labels include hydrolases, particularly esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinedioners, e.g., luminol.

Using the method and kit of the present invention, live microorganisms (particularly bacteria, protozoa, mold, and yeast) present in chlorine- or bromine-treated water are collected from the water by filtration or other appropriate means and then treated with a lysing solution to expose the microorganism's DNA or RNA. For bacteria, lysing is typically carried out using a lysozyme, typically chicken egg white lysozyme, followed by a series of quick freezing and thawing steps or by treatment with a surfactant to disrupt the cell membrane. For protozoa, the nucleic acid therefrom is suitably exposed using a protease, such as proteinase K or by phenol extraction. After lysing, and prior to hybridization, target DNA can be amplified using a polymerase chain reaction to increase sensitivity of the test. A method for target DNA amplification was disclosed in U.S. Pat. No. 4,683,195 and 4,683,202. Steffan et al, "DNA Amplification to Enhance Detection of Genetically Engineered Bacteria in Environmental Samples", Appl. Environ. Microbiol., 54; pp. 2185-91 (1988) demonstrated that this amplification method is applicable to environmental samples, and found that as little as one microorganism per gram of sediment could be detected after amplification. Steffan et al. demonstrated that this amplification method is applicable to environmental samples, and found that as little as one microorganism per gram of sediment could be detected after amplification. After lysing, the released nucleic acid is rendered single-stranded by heating, and the single-stranded nucleic acid from the various microorganisms (some of which may be target nucleic acid from undesirable or indicator microorganisms) is contacted with single-stranded probe nucleic acid for possible hybridization thereof.

As indicated above, suitable first and second probe segments have base sequences that are complementary to base sequences on undesirable (e.g., potentially harmful) or indicator microorganisms that may be present in chlorine- or bromine-treated water.

In the hybridization, the single-stranded target nucleic acid derived from microorganisms in a chlorine- or bromine-treated water sample is reacted with the probe under conditions where hybridization of the probe with the target microorganism DNA can occur.

The particular hybridization technique employed is not a critical element of the present invention. Various hybridization solutions may be employed, comprising from about 20 to 60, preferably 40 to 50, volume percent of an inert polar organic solvent. A common hybridization solution employs about 50 percent formamide, about 0.05 to 0.5M sodium phosphate, and minor amounts of EDTA. Alternatively, aqueous solutions containing these salts and free of organic solvents such as formamide may be employed. The hybridization time employed can be one-half hour or less up to several hours or more as desired.

The extent of hybridization is affected by various factors, including temperature, probe concentration, probe length, ionic strength, time, and the like. As an illustrative example, the extent of hybridization can be varied by changing the polarity of the reactant solution by manipulating the concentration of formamide in the range of 0 to 50 percent. Alternatively, temperatures can be varied in the range of about 20° to 85° C., usually 30° to 75° C.

In carrying out the method of the present invention, a sample of chlorine- or bromine-treated water suspected of containing the microbe(s) is provided from, for example, a drinking water testing station. Microorganisms in the sample may have been pre-concentrated by using parallel flow or perpendicular flow filters. After lysing the microbe(s) and treating the released nucleic acid to render it single-stranded, such as by heating, the single-stranded target DNA or RNA material is then hybridized with two labelled probe polynucleotides having a complementary base sequence to mutually exclusive portions of the target nucleic acid.

The amount of labelled probe utilized in the hybridization solution will vary widely, depending upon the nature of the label, and the stringency of the hybridization. Preferably, substantial excesses over a stoichiometric amount of the probe relative to the amount of the known-sequence target to be hybridized will be employed in order to enhance the rate of hybridization and to allow the quantifying of the amount of target sequences present. For example, a 100 fold to 1,000 fold excess of probe to specific target sequences will allow rapid hybridization of all target sequences. Such an excess also allows quantitative analysis of numbers of contaminating organisms in a single test.

As stated above, the kit of the present invention contains a sample of labelled probe, a lysing medium, and a detection means for identifying said detection signal. Illustrative instrumentation useful for signal detection includes a photomultiplier tube for measuring light emitted and, preferably, filters to remove background chemiluminescence. Typically, the sample live indicator or undesirable (target) microorganisms in or obtained from chlorine- or bromine-treated water will be provided by the kit user. The kit also preferably contains a hybridization buffer solution for optimizing hybridization of labelled probe nucleic acid with target nucleic acid. If the probe is enzyme labelled, the kit also preferably contains an enzyme substrate and buffer solution to optimize the enzyme's catalytic activity and to allow signal development and/or enhancement of the label for identification of the hybridized probe/target nucleic acid molecules.

The method and kit of the present invention are especially useful for detecting the presence of live indicator or undesirable microorganisms in chlorine-treated or bromine-treated drinking or waste water and other chlorine-treated or bromine-treated water for human or animal consumption, such as water for use in foods or chlorine-treated or bromine-treated water used for bathing or recreational purposes.

The following example is intended to illustrate, but in no way limit the scope of, the present invention.

PROPOSED EXAMPLE

Nucleic Acid Probe Synthesis

Nucleic acid probe preparation is described in U.S. Pat. No. 4,670,379, issued June 2, 1987 to J. A. Miller in each of the examples that patent discloses. In brief, two nucleic acid probes are synthesized that are complementary to two adjacent, non-overlapping sequences on the target nucleic acid such that when the two probes hybridize with the target there are from 1 to 50 nucleotides from the 3' terminal of one probe to the 5' terminal of the other probe, the optimal being 10 nucleotides. Conjugated near the 3' (or 5') end of one probe would be an enzyme or other catalyst capable of forming a transformation radical. This transformation radical could then convert an apoluminescer conjugated to the other probe; that is, when both probes are hybridized to the target nucleic acid molecule. Alternatively, the probes are constructed as described in European patent application No. 0 070 685, published Jan. 26, 1983 to Heller et al. In this case, the probes are made as above except that conjugate near the 3' (or 5') end of one probe is a chemiluminescent catalyst. Conjugated near the 5' (or 3') end of the other probe is an absorber/emitter moiety. When the two probes hybridize to the target nucleic acid the chemiluminescent catalyst and the absorber/emitter moiety are close enough to allow non-radiative energy transfer. Signal generation consists of exciting one moiety, which emits light at a wavelength absorbed by the second moiety. If the two moieties are sufficiently close, i.e., when the probes are hybridized to the target nucleic acid, the second moiety emits light at a different wavelength, which is measured.

Illustrative Method for Target DNA Preparation

Crude Extracts Without Centrifugation

It is possible to make crude extracts to provide target nucleic acid sequences. This is the preferred method since it simplifies the steps required before hybridization. A cell suspension is made of cells collected by filtration or other means from a water sample. Cells are next lysed using the following two-step procedure:

Step (A) A cell suspension is made in 800 ml. of lysis buffer (0.125M phosphate buffer pH=6.8, 10mM EDTA) which has been prewarmed to 37° C.; vortex. Add 100 ul of 20 mg/ml lysozyme in lysis buffer; vortex. Incubate at 37° C. for 30 minutes.

Step (B) Add 100 ul of Protease K (BRL Cat. # 5530UA) at 5 mg/ml in lysis buffer. Vortex and incubate at 37° C. for 45 minutes; place tube in boiling water bath and boil for three minutes.

Target DNA Amplification Prior to Hybridization

Saiki et al, "Enzymatic Amplification of B-globin Genomic Sequences and Restriction Site Analysis for Diagnosis of Sickle Cell Anemia", Science, 230; pp. 1350-54 (1985); M. B. Mullis, U.S. Pat. No. 4,683,202, issued July 28, 1987; and Mullis et al, U.S. Pat. No. 4,683,195, issued July 28, 1987; describe how to amplify specific target sequences prior to hybridization in order to enhance probe sensitivity. This amplification step can be inserted into the protocol by adding the amplification materials and procedures after lysis (Step (B) above) and before hybridization. The materials needed include extension primers which are small oligonucleotide polymers that hybridize to the target DNA on sites flanking the probe hybridization site. Also required is Taq polymerase, a heat stable DNA polymerase isolated from the thermophilic baterium *Thermus aquaticus*. Briefly, the amplification protocol is:

1. Heat-denature the target DNA sequence in the presence of extension primers, deoxyribonucleoside triphosphates (dNTPs), reaction buffer, and Taq polymerase.
2. Anneal the oligonucleotide primer to the denatured template by lowering the temperature.
3. Extend the primer with Taq polymerase.
4. Start denaturing the amplification product by returning to step 1. Repeat cycle 25 times.

Hybridization Reaction

Adjust solution to 0.48M phosphate buffer pH=6.8, 10m MEDTA, warm to 50° C. and add 54 ug of each probe. Vortex. Incubate for hybridization for one hour at 22° C. The presence of specific target sequences that hybridize with the two probe nucleic acid molecules is verified by adding substrate for the catalyst and then exciting the sample in a microcuvette at 500 nm and observing the resulting 520 nm emission.

Kit Components

The materials utilized in the above-described method are suitably provided in a packaged combination of containers holding the necessary reagents for detecting the presence of waterborne microorganisms. The kit includes;

1. probes specific for the microorganism of interest such that the probes hybridize to two adjacent, non-overlapping nucleic acid sequences found only in the target microorganism; the probes are conjugated with a signal system as described above in "Nucleic acid probe synthesis" as specified in U.S. Pat. No. 4,670,379 and European Pat. No. 0 070 685;
2. reagents for signal regeneration;
3. lysis reagents;
   (a) 0.0125M phosphate buffer pH=6.8, 10mM EDTA,
   (b) above buffer containing 20 mg/ml lysozyme,
   (c) above buffer containing 5 mg/ml Protease K;
4. hybridization buffers, 2M phosphate buffer pH=6.8, 10mM EDTA;
5. if DNA amplification is employed -
   (a) extension primers,
   (b) dNTPs
   (c) reaction buffer
   (d) Taq polymerase.

WHAT IS CLAIMED IS:

1. A method for detecting the presence of live microorganisms in a mixture of live and dead microorganisms in chlorine- or bromine-treated water comprising:
   (a) lysing live microorganisms present in a sample of chlorine- or bromine-treated water and rendering constituent nucleic acid molecules single-stranded to provide a single-stranded target polynucleotide;
   (b) contacting said single-stranded target polynucleotide, under hybridization conditions, with first and second probe labels which are complementary to mutually exclusive portions of said single-stranded polynucleotide to cause hybridizaton between said single-stranded target polynucleotide and said first and second single-stranded labelled probe nucleic acid segments, said first and second single-stranded labelled probe nucleic acid segments cooperating after said hybridization to generate a detection signal, and
   (c) detecting said detection signal to permit identification of said hybridization, whereby a positive detection signal evidences the presence of said live microorganisms in said sample.

2. The method of claim 1 wherein said labels on first and second single-stranded probe nucleic acid segments cooperate in Step (b) to generate a chemiluminescent signal.

3. The method of claim 2 wherein said chemiluminescent signal is detected in Step (c) by measuring emitted light by means of a photomultiplier tube.

4. The method of claim 1 wherein said first and second single-stranded labelled probe nucleic acid segments are labelled respectively with a catalyst-label and a luminescer-label or with two luminescer-labels.

5. The method of claim 1 wherein said first and second single-stranded labelled probe nucleic acid segments are labelled with a catalyst-label and a chemiluminescent-label, respectively.

6. The method of claim 1 wherein said first and second single-stranded labelled probe nucleic acid segments are labelled with a catalyst-label and an apoluminscer label, respectively.

7. A kit for detecting the presence of live microorganisms in chlorine- or bromine-treated water comprising:
   (a) a sample of live microorganisms in, or obtained from, chlorine- or bromine-treated water,
   (b) a lysing medium for providing a single-stranded target polynucleotide from within live microorganisms isolated from chlorine- or bromine-treated water,
   (c) first and second single-stranded labelled probe nucleic acid segments which are complementary to mutually exclusive portions of said single-stranded target polynucleotide, said first and second probe labels being adapted to cooperate to generate a detection signal after hybridization with said single-stranded target polynucleotide, and
   (d) detection means for identifying said detection signal, whereby a positive detection signal evidences the presence of said live microorganisms in said sample.

8. The kit of claim 7 wherein said detection means is a photomultiplier tube.

9. The kit of claim 7 which additionally contains at least one light filter.

10. The kit of claim 7 which additionally contains a hybridization solution to facilitate rapid hybridization of probe nucleic acid with target nucleic acid.

* * * * *

UNITED STATES PATENT AND TRADEMARK OFFICE
CERTIFICATE OF CORRECTION

PATENT NO. : 4,983,511
DATED : January 8, 1991
INVENTOR(S) : Geiger et al

It is certified that error appears in the above—identified patent and that said Letters Patent is hereby corrected as shown below:

In Column 10, at line 12 after "isms" and before "in" insert --in a mixture of live and dead microorganisms--.

Signed and Sealed this

Eleventh Day of August, 1992

Attest:

DOUGLAS B. COMER

*Attesting Officer*   *Acting Commissioner of Patents and Trademarks*